United States Patent
Grashow et al.

(10) Patent No.: US 11,351,318 B2
(45) Date of Patent: Jun. 7, 2022

(54) PRESSURE SUPPORT DEVICE AND METHOD OF DETERMINING CHANGES IN A PATIENT CIRCUIT

(71) Applicant: KONINKLIJKE PHILIPS N.V., Eindhoven (NL)

(72) Inventors: Jonathan Sayer Grashow, Pittsburgh, PA (US); Benjamin Irwin Shelly, Pittsburgh, PA (US); Michael Thomas Kane, Harrison City, PA (US); Robert William Baiko, Pittsburg, PA (US)

(73) Assignee: Koninklijke Philips N.V., Eindhoven (NL)

( * ) Notice: Subject to any disclaimer, the term of this patent is extended or adjusted under 35 U.S.C. 154(b) by 219 days.

(21) Appl. No.: 16/472,489

(22) PCT Filed: Dec. 21, 2017

(86) PCT No.: PCT/EP2017/083966
§ 371 (c)(1),
(2) Date: Jun. 21, 2019

(87) PCT Pub. No.: WO2018/115216
PCT Pub. Date: Jun. 28, 2018

(65) Prior Publication Data
US 2019/0321573 A1     Oct. 24, 2019

Related U.S. Application Data
(60) Provisional application No. 62/438,503, filed on Dec. 23, 2016.

(51) Int. Cl.
*A61M 16/00* (2006.01)
*A61M 16/06* (2006.01)
*A61M 16/08* (2006.01)

(52) U.S. Cl.
CPC .... *A61M 16/0003* (2014.02); *A61M 16/0066* (2013.01); *A61M 16/06* (2013.01);
(Continued)

(58) Field of Classification Search
CPC .......... A61M 16/0003; A61M 16/0066; A61M 16/0069; A61M 16/06; A61M 16/00;
(Continued)

(56) References Cited

U.S. PATENT DOCUMENTS

| 7,115,097 B2 | 10/2006 | Johnson |
| 8,766,790 B2 | 7/2014 | Jacob |

(Continued)

FOREIGN PATENT DOCUMENTS

| JP | 2007502670 A | 2/2007 |
| WO | WO2011151739 A1 | 12/2011 |

(Continued)

OTHER PUBLICATIONS

PCT International Search Report, International application No. PCT/EP2017/083966, dated Feb. 26, 2018.

*Primary Examiner* — Joseph D. Boecker
*Assistant Examiner* — Thomas W Greig
(74) *Attorney, Agent, or Firm* — Michael W. Haas (57) ABSTRACT

A pressure support device for providing pressure support therapy to a patient includes an airflow generator structured to generate pressure to provide pressure compensation to the patient via a patient circuit, one or more sensors structured to gather data related to effectiveness of the pressure compensation, and a processing unit structured to analyze outputs of the sensors while pressure support therapy is provided to the patient to determine if the pressure compensation provided to the patient is improper and to initiate action to confirm whether components of the patient circuit have been changed in response to determining that (Continued)

the pressure compensation provided to the patient is improper.

12 Claims, 4 Drawing Sheets

(52) U.S. Cl.
CPC ..... *A61M 16/08* (2013.01); *A61M 2016/0027* (2013.01); *A61M 2205/3331* (2013.01); *A61M 2205/50* (2013.01)

(58) Field of Classification Search
CPC .. A61M 2016/0015; A61M 2016/0018; A61M 2016/0021; A61M 16/08; A61M 16/0816; A61M 16/0875; A61M 16/0883; A61M 16/0891
See application file for complete search history.

(56) References Cited

U.S. PATENT DOCUMENTS

| | | |
|---|---|---|
| 8,789,528 B2 | 7/2014 | Carter |
| 2005/0061319 A1 | 3/2005 | Hartley |
| 2005/0061320 A1 | 3/2005 | Lee |
| 2006/0096596 A1 | 5/2006 | Occhialini |
| 2009/0050154 A1* | 2/2009 | Strothmann ...... A61M 16/0069 128/204.23 |
| 2010/0147303 A1 | 6/2010 | Jafari |
| 2010/0186741 A1 | 7/2010 | Aylsworth |
| 2011/0061647 A1* | 3/2011 | Stahmann ............ A61B 5/0031 128/202.16 |
| 2012/0157794 A1 | 6/2012 | Goodwin |
| 2012/0215125 A1* | 8/2012 | Orr ...................... G01N 33/497 600/532 |
| 2012/0229272 A1* | 9/2012 | Jacob ................... A61M 16/00 340/539.12 |
| 2015/0090258 A1 | 4/2015 | Milne |
| 2015/0144130 A1 | 5/2015 | O'Donnell |
| 2016/0256642 A1* | 9/2016 | Soysa ............... A61M 16/0051 |
| 2016/0354567 A1 | 12/2016 | Grashow |

FOREIGN PATENT DOCUMENTS

| | | |
|---|---|---|
| WO | WO2011151741 A1 | 12/2011 |
| WO | WO2015179917 A1 | 12/2015 |

* cited by examiner

PRESSURE SUPPORT DEVICE AND METHOD OF DETERMINING CHANGES IN A PATIENT CIRCUIT

CROSS-REFERENCE TO RELATED APPLICATIONS

This patent application claims the priority benefit under 35 U.S.C. § 371 of international patent application no. PCT/EP2017/083966, filed Dec. 21, 2017, which claims the priority benefit under 35 U.S.C. § 119(e) of U.S. Provisional Application No. 62/438,503, filed on Dec. 23, 2016, the contents of which are herein incorporated by reference.

BACKGROUND OF THE INVENTION

1. Field of the Invention

The present invention pertains to a pressure support device, and, in particular, to a pressure support device including one or more sensors to detect improper pressure compensation.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive airway pressure (PAP) to the patient's airway using an airway pressure support system that typically includes a mask, a pressure generating device, and a conduit to deliver positive pressure breathing gas from the pressure generating device to the patient through the mask. This positive pressure effectively "splints" the airway, thereby maintaining an open passage to the lungs. In one type of PAP therapy, known as continuous positive airway pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

The mask, conduit, and generally other components between the pressure generating device and the patient are typically considered to be the patient circuit. The settings of the pressure generator are calibrated based on the type of components used in the patient circuit. For example, the pressure generating device may generate a particular pressure when a selected type of mask and conduit are used in the patient circuit. However, if the pressure generating device generates the same particular pressure, but a different type of mask and conduit are used in the patient circuit, the pressure support therapy provided to the patient may not be effective. The settings of the pressure generating device should be updated each time a component of the patient circuit is changed. While a technician or medical provider may be aware that settings of the pressure support generator should be updated each time a component of the patient circuit is changed, a typical patient may not be aware of this need.

SUMMARY OF THE INVENTION

A pressure support device for providing pressure support therapy to a patient comprises: an airflow generator structured to generate pressure to provide pressure compensation to the patient via a patient circuit; one or more sensors structured to gather data related to effectiveness of the pressure compensation; and a processing unit structured to analyze outputs of the sensors while pressure support therapy is provided to the patient to determine if the pressure compensation provided to the patient is improper and to initiate action to confirm whether components of the patient circuit have been changed in response to determining that the pressure compensation provided to the patient is improper.

A method of determining changes in a patient circuit comprises: receiving data from one or more sensors structured to gather data related to effectiveness of pressure compensation provided to a patient from an airflow generator via the patient circuit in the course of pressure support therapy; analyzing outputs of the sensors while pressure support therapy is provided to the patient; determining if the pressure compensation provided to the patient is improper; and if the pressure compensation provided to the patient is determined to be improper, initiating action to confirm whether components of the patient circuit have been changed.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
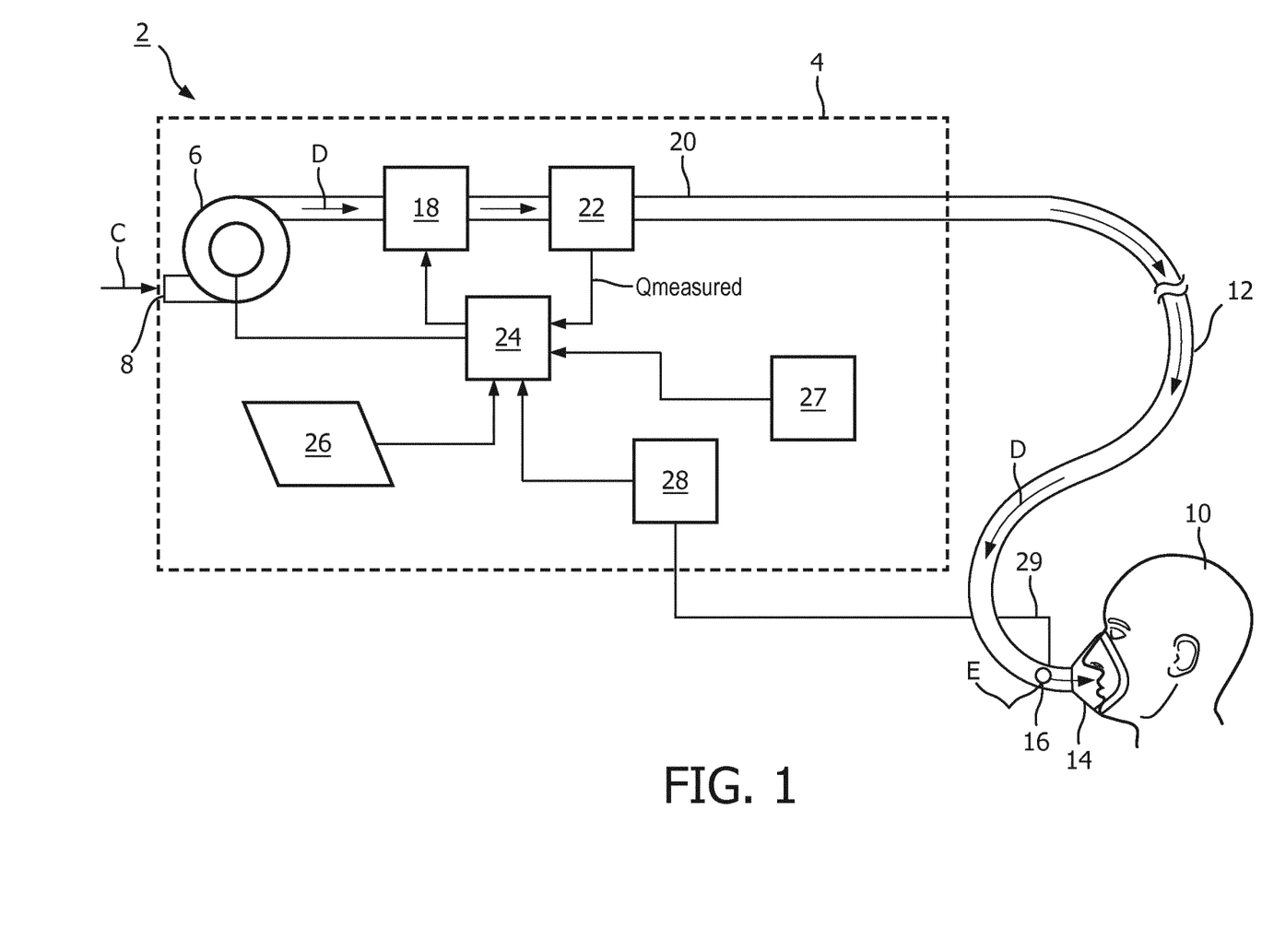
FIG. 1 is a schematic diagram of a pressure support system adapted to provide a regimen of respiratory therapy to a patient according to an exemplary embodiment of the disclosed concept.

FIG. 1 is a schematic diagram of an airway pressure support system 2 according to one particular, non-limiting exemplary embodiment in which the present invention may be implemented. Referring to FIG. 1, airway pressure support system 2 includes a pressure support device 4 which houses a gas flow generator 6, such as a blower used in a conventional CPAP or bi-level pressure support device. Gas flow generator 6 receives breathing gas, generally indicated by arrow C, from the ambient atmosphere through a filtered air inlet 8 (described in greater detail herein) provided as part of pressure support device 4, and generates a flow of breathing gas therefrom for delivery to an airway of a patient 10 at relatively higher and lower pressures, i.e., generally equal to or above ambient atmospheric pressure. In the exemplary embodiment, gas flow generator 6 is capable of providing a flow of breathing gas ranging in pressure from 3-30 cm H2O. The pressurized flow of breathing gas from gas flow generator 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as a patient circuit.

Pressure support system 2 shown in FIG. 1 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as in patient interface device 14. It should also be understood that exhaust vent 16 can have a wide variety of configurations depending on the desired manner in which gas is to be vented from pressure support system 2. Together, delivery conduit 12 and patient interface device 14 are referred to as the patient circuit.

The present invention also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in a housing of pressure support device 4. Valve 18 controls the pressure of the flow of breathing gas from gas flow generator 6 that is delivered to patient 10. For present purposes, gas flow generator 6 and valve 18 are collectively referred to as a pressure generating system because they act in concert to control the pressure and/or flow of gas delivered to patient 10. However, it should be apparent that other techniques for controlling the pressure of the gas delivered to patient 10, such as varying the blower speed of gas flow generator 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to gas flow generator 6 alone, and the pressure of gas in the patient circuit is controlled, for example, by controlling the motor speed of gas flow generator 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Pressure support system 2 additionally includes a pressure sensor 27 that detects the pressure of the pressurized fluid in delivery conduit 20. While the point at which the flow is measured by flow sensor 22 and the pressure is measured by pressure sensor 27 are illustrated as being within pressure support device 4, it is to be understood that the location at which the actual flow and pressure measurements are taken may be anywhere along delivery conduits 20 or 12. The flow of breathing gas measured by flow sensor 22 and the pressure detected by pressure sensor 27 are provided to processing unit 24 to determine the flow of gas at patient 10 ($Q_{PATIENT}$).

Techniques for calculating $Q_{PATIENT}$ are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow, and using this determination in calculating $Q_{PATIENT}$ using measured flow and pressure. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 18.

In some non-limiting embodiments of the disclosed concept, pressure support system 2 also includes a proximal pressure sensor 28 that is in fluid communication with a point along delivery conduit 12. For example and without limitation, proximal pressure sensor 28 may be in fluid communication with a point on delivery conduit 12 near patient interface device 14 via a probe 29 connected between proximal pressure sensor 28 and the point on delivery conduit 12. Proximal pressure sensor 28 facilitates measuring pressure proximate the point on delivery conduit 12 and provide the measured proximal pressure to processing unit 24. It will be appreciated that in some exemplary embodiments, proximal pressure sensor 28 may be omitted.

While the flow sensor 22, pressure sensor 27, and proximal pressure sensor 28 have been shown in conjunction with the pressure support system 2 illustrated in FIG. 1, it will be appreciated by those having ordinary skill in the art that other types of sensors may also be employed in conjunction with pressure support system 2 without departing from the scope of the disclosed concept. For example and without limitation, a temperature sensor may be used to measure temperature, a proximity/contact sensor may be used to sense contact between patient 10 and components of the patient interface. Other types of sensors that may be employed in conjunction with pressure support system include, for example and without limitation, location sensors (e.g., global positioning system sensors) to determine a location of pressure support system 2, light sensors to sense light, accelerometers 29 (shown in FIG. 2) to sense acceleration and/or movement, microphones to sense sound, or identification sensors such as radio frequency identification (RFID) sensors to sense identification information from RFID chips attached to components. It will be appreciated that the foregoing examples of types of sensors that may be employed in conjunction with pressure support system 2 is not exhaustive and other types of sensors may also be employed without departing from the scope of the disclosed concept.

Processing unit 24 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2. Processing unit 24 is structured to receive outputs of one or more sensors structured to gather data related to effectiveness of the pressure support therapy. An example of such a sensor is flow sensor 22. However, other types of sensors may also gather data related to effectiveness of the pressure support therapy and be employed with processing unit 24, as will be described in more detail herein. Processing unit 24 is also structured to analyze outputs of the sensors while pressure support therapy is provided to the patient to determine if the pressure compensation provided to the patient is improper. If the pressure compensation provided to the patient is determined to be improper, the processing unit 24 is structured to initiate action to confirm whether components of the patient circuit have been changed.

An input/output device 26 is provided for setting various parameters used by airway pressure support system 2, as well as for displaying and outputting information and data to a user, such as a clinician or caregiver.

It will be appreciated that pressure support device 4 may include additional components that are not illustrated in the schematic diagram of FIG. 1. For example and without limitation, pressure support device 4 may include a filter to filter breathing gas provided to patient 10 and a humidifier to humidify breathing gas provided to patient 10.

In the illustrated, non-limiting exemplary embodiment of the present invention, airway pressure support system 2 essentially functions as a CPAP pressure support system and pressure support device 4 provides functions of a CPAP base unit. Pressure support system 2, therefore, includes all of the capabilities necessary in such systems in order to provide appropriate CPAP pressure levels to patient 10. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 2:
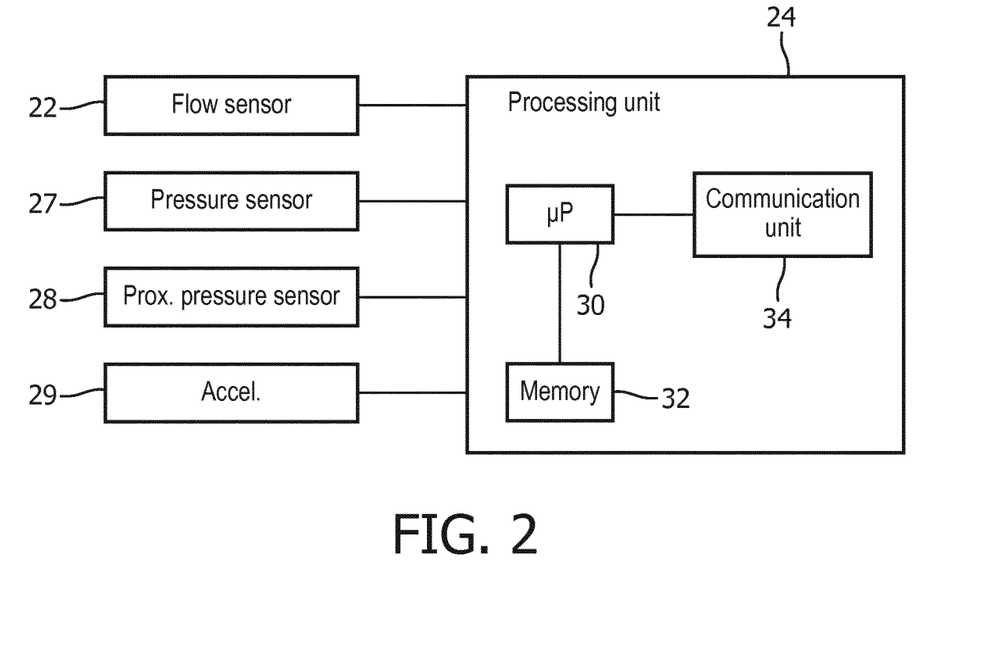
FIG. 2 is a schematic diagram of a processing unit according to an exemplary embodiment of the disclosed concept.

FIG. 2 is a block diagram of processing unit 24 in accordance with a non-limiting exemplary embodiment of the disclosed concept. Processing unit 24 includes a processor 30, a memory 32, and a communication unit 34. Processor 30 may form all or part of a processing portion which may be, for example, a microprocessor, a microcontroller or some other suitable processing device. Memory 32 may form all or part of a memory portion that may be internal to the processing portion or operatively coupled to the processing portion and provide a storage medium for data and software executable by the processing portion for implementing functionality of processing unit 23 and controlling the operation of pressure support system 2. Memory 32 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory.

Communication unit 34 may provide for communication between processing unit 24 and other components of pressure support device 4, components of the patient circuit, or other external devices. For example and without limitation, communication unit 34 may facilitate communication with various sensors such as flow control sensor 22. Communication unit 34 may also facilitate communication with external devices. For example and without limitation, communication unit 34 may facilitate communication with electronic devices such as a phone, tablet, computer, or other devices directly or via a network. Communication facilitated by communication unit 34 may allow processing unit 24 to send and/or receive data from the component or device it communicates with.

As previously described, processing unit 24 receives outputs from one or more sensors such as, for example and without limitation, flow sensor 22, pressure sensor 27, proximal pressure sensor 28, and accelerometer 29. Although flow sensor 22, pressure sensor 27, proximal pressure sensor 28, and accelerometer 29, it will be appreciated that one or more of these sensors may be omitted without departing from the scope of the disclosed concept. It will also be appreciated that processing unit 24 may receive outputs from one or more other types of sensors that are not shown in FIG. 2. For example and without limitation, processing unit 24 may receive outputs from one or more of a temperature sensor, a proximity/contact sensor, location sensors, microphones, or identification sensors.

Figure 3:
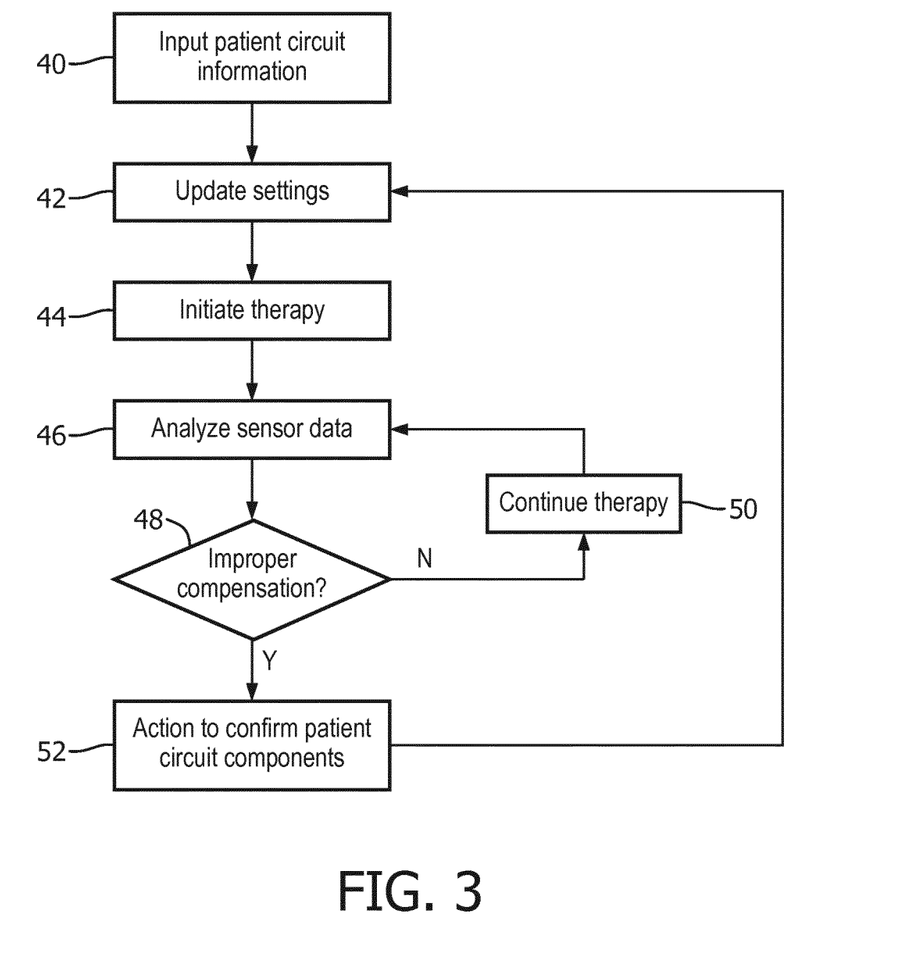
FIG. 3 is a flowchart of a method of determining improper compensation according to an exemplary embodiment of the disclosed concept.

FIG. 3 is a flowchart of a method of determining improper compensation in accordance with a non-limiting exemplary embodiment of the present invention. The method of FIG. 3 may be employed in, for example, pressure support system 2. At 40, patient circuit information is input to pressure support device 4. The patient circuit information may include various information about components of the patient circuit such as delivery conduit 12 and patient interface 14. The patient circuit information may include information such as, without limitation, mask type, mask resistance, hose type, hose length, filter type, humidifier type, etc. Once the patient circuit information is input to pressure support device 4, it may be stored, for example, in memory 32 of processing unit 24.

The patient circuit information may be input to pressure support system 2 in any suitable manner. For example, in one non-limiting exemplary embodiment of the disclosed concept, the patient circuit information may be input to pressure support system 2 manually by a patient, medical provider, or other user through input/output device 26, where it is then communicated to processing unit 24. In another non-limiting exemplary embodiment of the disclosed concept, one or more components of the patient circuit may include memory to store their corresponding information. The patient circuit information stored in the components of the patient circuit may be transmitted to processing unit 24. In some exemplary embodiments of the disclosed concept, the patient circuit information is wirelessly transmitted from components of the patient circuit to processing unit 24.

In yet another exemplary embodiment of the disclosed concept, the patient circuit information may be stored in an external database. For example and without limitation, a medical provider may input the patient circuit information (e.g., the mask type, mask resistance, hose type, etc.) for the patient circuit components used in pressure support system 2. Identification information such as an identification number may be used to associate the patient circuit information with a particular pressure support device 4. The patient circuit information may then be transmitted from the external database to processing unit 24. In some exemplary embodiments of the disclosed concept, processing unit 24 may query the external database and receive the patient circuit information in response.

At 42, settings of pressure support device 4 are updated based on the patient circuit information. In one non-limiting exemplary embodiment, settings related to pressure compensation provided by pressure support device 4 and/or alarm thresholds for pressure support device 4 are updated based on the patient circuit information. The settings related to pressure compensation may include settings for controlling airflow generator 6 (e.g., without limitation, impeller speed) and/or valve 18. Variations in types and sizes of patient circuit components affect operational parameters of components of the patient circuit such as airflow resistance, airflow exhaust, compliance, and airflow inductance. Failing to update settings of pressure support device 4 based on the patient circuit information can result in sub-optimal performance.

At 44, pressure support device 4 begins providing pressure support therapy to the patient by, for example, controlling airflow generator 6 and/or valve 18 to generate and provide pressure compensation to patient 10. The pressure support therapy may be any of a variety of known pressure support therapies.

At 46, processing unit 24 analyzes sensor data related to the effectiveness of the pressure compensation provided to patient 10. The sensor data may be gathered from one or more different sensors such as flow sensor 22. At 48, processing unit 24 determines whether the pressure compensation provided to patient 10 is improper.

Exacerbation of sleep disordered breathing symptoms is one type of indication that the pressure compensation provided to patient 10 is improper. An increase in the frequency of snoring and obstructive hypopnea are two examples of an exacerbation of sleep disordered breathing symptoms. In one non-limiting embodiment of the disclosed concept, processing unit 24 receives data from sensors structured to gather data related to exacerbation of sleep disordered breathing symptoms. Flow sensor 22 and pressure sensor 27 provide data related to exacerbation of sleep disordered breathing symptoms and exacerbation of sleep disordered breathing symptoms may be detected by analyzing outputs of flow sensor 22 and pressure sensor 27. In exemplary embodiments of the disclosed concept, various other types of sensors may also be employed in pressure support system to provide data related to exacerbation of sleep disordered breathing symptoms. For example and without limitation, electrical sensors used in conjunction with performing an electrocardiogram (EKG), an electroencephalogram (EEG), or an electromyography (EMG) may be employed to provide data related to exacerbation of sleep disordered breathing symptoms. Microphones, cameras, oxygen and carbon dioxide sensors, an effort belt, accelerometers, or ultrasonic sensors may also be employed to provide data to provide data related to exacerbation of sleep disordered breathing. Moreover, any sensor used in conjunction with a polysomnogram may be employed to provide data related to exacerbation of sleep disordered breathing may be employed without departing from the scope of the disclosed concept. The examples of sensors that provide data related to exacerbation of sleep disordered breathing conditions above is not exhaustive and it will be appreciated that any sensor that provide data related to a data used to detect exacerbation of sleep disordered breathing symptoms may be employed without departing from the scope of the disclosed concept.

Processing unit 24 then analyzes the data related to exacerbation of sleep disordered breathing symptoms and determines whether the pressure compensation to patient 10 is improper. Processing unit 24 may determine that the pressure compensation to patient 10 is improper based on, for example, the severity and/or frequency of the exacerbation of sleep disordered breathing symptoms.

A sub-optimal breath waveform shape is another indication that pressure compensation provided to patient 10 is improper. For example, a mismatch between the actual airflow resistance of a patient circuit component and the resistance value input into airflow generator 6 can cause airflow generator 6 to miscalculate the blower output required to maintain comfortable breathing for patient 10. A sub-optimal breath waveform shape may be indicated by signs of uncomfortable breathing such as expiratory tails, flow limited peak inspiration, lengthened I-E ratio, and/or pressure oscillations.

In a non-limiting exemplary embodiment of the disclosed concept, processing unit 24 receives data from sensors structured to gather data related to a sub-optimal waveform shape. Flow sensor 22 and/or pressure sensor 27 provide data related to a sub-optimal waveform shape. Processing unit 24 then analyzes the data related to a sub-optimal waveform and determines whether the pressure compensation to patient 10 is improper. Processing unit 24 may determine that the pressure compensation to patient 10 is improper based on, for example, the frequency and/or severity of signs of uncomfortable breathing.

Figure 4A:
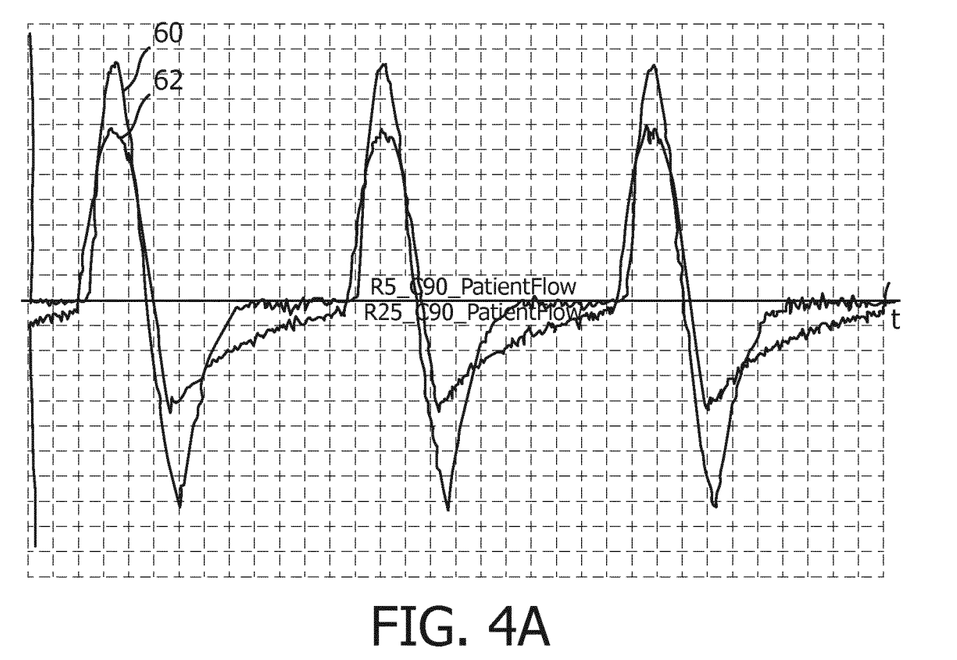
FIGS. 4A and 4B are examples of waveform shapes.
Figure 4B:
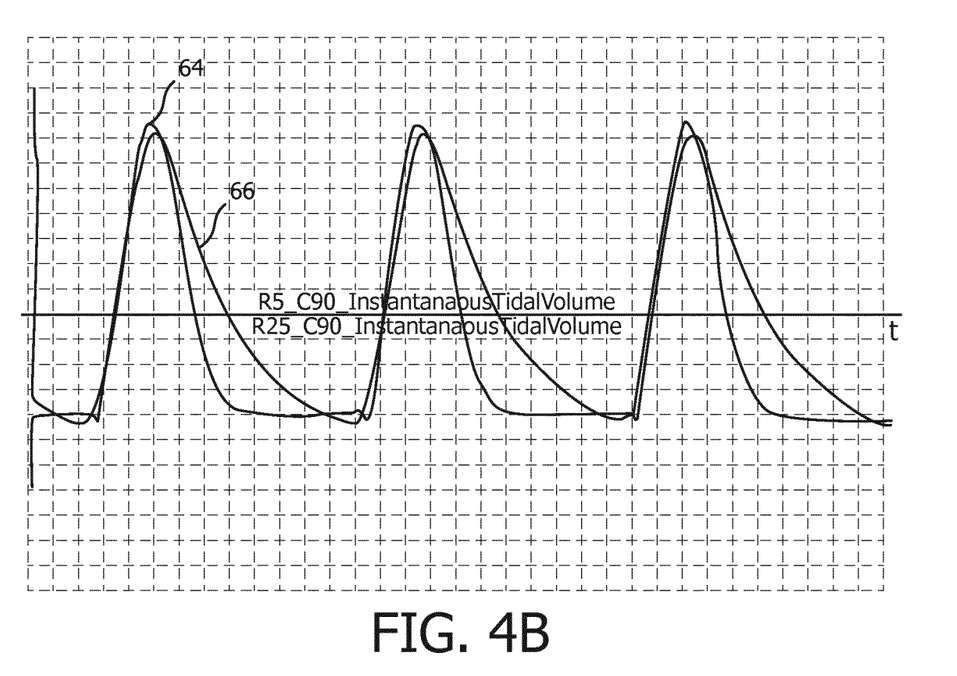

FIGS. 4A and 4B are examples of waveform shapes. FIG. 4A is a graph of $Q_{PATIENT}$ for two different breathing time constants. The lung parameters used in a first plot 60 are R5C90 in a spontaneous breathing pattern with a muscle effort of −8 cm H2O. The parameters in a second plot 62 are R25C90 with a Pmus of −15. Both conditions reach a similar peak value at around the same time of inspiration. However, due to the difference in lung resistance, the time constant of expiration is long in the second plot 62.

FIG. 4B is a graph of instantaneous change in lung volume corresponding to the $Q_{PATIENT}$ waveforms shown in FIG. 4A. FIG. 4B includes a third plot 64 which corresponds to the first plot 60 in FIG. 4A. FIG. 4B also includes a fourth plot 66 which corresponds to the second plot 62 in FIG. 4A.

Classic ventilation parameters have been used to describe the $Q_{PATIENT}$ waveform. Some examples of such parameters are inspired tidal volume (Vti), expired tidal volume (Vte), inspiration time (Itime), expiration time (Etime), the minimum value during expiration (Qmin), and the maximum value during inspiration (Qmax). These example parameters may be determined from the waveform shapes shown in FIGS. 4A and 4B. Table 1 shows values for some classic ventilation parameters for the waveforms of FIGS. 4A and 4B.

TABLE 1

|  | Vti | Vte | Itime | Etime | Qmin | Qmax |
|---|---|---|---|---|---|---|
| R25C90 | 672.9 | −663.5 | 2.4 | 6.2 | −16.6 | 26.8 |
| R5C90 | 696.9 | −671.8 | 1.9 | 3.2 | −31.4 | 36.2 |

Advanced parameters may also be determined from the waveforms of FIGS. 4A and 4B. For example, $Q_{PATIENT}$ is first calculated as a function of tidal volume. Then the maximum value of $Q_{PATIENT}$ is determined and $Q_{PATIENT}$ is normalized for the tidal volume of the breath by dividing the maximum of $Q_{PATIENT}$ by the inspired tidal volume. The resultant parameter is indicated in Table 2A by PkFl_Vte and may be used in determining whether signs of uncomfortable breathing are present. A similar advanced parameter may be calculated for expiratory flow by dividing the minimum value of $Q_{PATIENT}$ by the expired tidal volume.

Other advanced parameters include inspired tidal volume divided by inspiration time (Vti/Tinsp), expired tidal volume divided by expiration time (Vte/Texp), the slope of the $Q_{PATIENT}$ waveform (Rise time), the change in $Q_{PATIENT}$ as a function of time (DQDT), the time constant of inspiration (TCi), which is how long it takes for the tidal volume to reach ⅔ of its maximum value, the time constant of expiration (TCe), which is how long it takes to reach ⅔ of the time of expiration, the ratio of TCi to TCe (TC ratio), the time in breath associated with Qmin (TimeQmin), and the peak flow divided by breath time (PkFl_BrTime). Some examples of advanced parameters corresponding to the waveforms of FIGS. 4A and 4B are shown in Tables 2A and 2B. The advanced parameters are useful in determining whether signs of uncomfortable breathing are present. For example, advanced parameters falling outside predetermined threshold levels may indicate uncomfortable breathing.

TABLE 2A

|  | PkFl_Vte | Vti/Tinsp | Rise Time | DQDT | TCi |
|---|---|---|---|---|---|
| R25C90 | −0.040 | 283.4 | 503.6 | 3.6 | 1.4 |
| R5C90 | −0.054 | 370.5 | 381.5 | 6.4 | 1.1 |

TABLE 2B

|  | TCe | TC Ratio | TimeQmin | PkFl_BrTime |
|---|---|---|---|---|
| R25C90 | 2.6 | 1.8 | 0.5 | 3.1 |
| R5C90 | 1.3 | 1.2 | 1.0 | 7.2 |

Referring back to FIG. 3, any of the classic ventilation parameters, the advanced parameters, any combination thereof, or other parameters, may be used by processing unit 24 to determine whether pressure compensation is improper due to signs of uncomfortable breathing being present.

In a non-limiting exemplary embodiment of the disclosed concept, processing unit 24 receives data from one or more sensors structured to sense pressure proximate to a component of the patient circuit. For example and without limitation, a pressure sensor may sense pressure proximal to a component such as patient interface 4. Processing unit 24 analyzes the data by, for example, comparing the pressure proximal to patient interface 4 to a predicted pressure proximal to patient interface 4. A mismatch between the measured pressure and the predicted pressure is an indication that the pressure compensation provided to patient 10 is improper and that parameters of the components used in the patient circuit may be different from the patient information settings of pressure support device 4 are based on. In a non-limiting example embodiment of the disclosed concept, processing unit 24 may determine improper pressure compensation is being provided to patient 10 when the difference between the measured pressure proximate to a component of patient circuit differs from a predicted pressure at that location by more than a predetermined threshold amount.

In another example embodiment of the disclosed concept, processing unit 24 receives sensor data from one or more sensors, such as accelerometers, structured to sense acceleration of patient 10 at one or more locations on patient 10.

Processing unit 24 associates the patient circuit information with an expected range of values of the one or more sensors. For example, if patient circuit information indicates that a patient circuit component includes an accelerometer at a particular location (e.g., at the top of patient's 10 head), the processing unit 24 may associate a range of expected values to be output from that accelerometer. If the location of the accelerometer is switched to a different location (e.g., around patient's 10 chest or abdominal area) and the patient circuit information is not updated in processing unit 24, the data received from the accelerometer is likely to fall outside the range of expected values. Processing unit 24 determining that data received from one or more sensors structured to sense acceleration of patient 10 is an indication that one or more components of the patient circuit have been changed and the pressure compensation provided to patient is improper.

While some examples of types of sensor data related to the effectiveness of pressure compensation provided to patient 10 have been described herein, it will be appreciated by those having ordinary skill in the art that any sensor data related to the effectiveness of pressure compensation may be used by processing unit 24 to determine whether pressure compensation provided to patient 10 is improper. For example, processing unit 24 may have associated expected ranges for various different types of data. The expected ranges may be predetermined or they may be determined based on historical data. For instance, if data from a sensor has a fairly constant value over a period of time, processing unit 24 may determine that the expected range of output from that sensor is around that constant value. If the output of that sensor then moves outside the expected range, the processing unit 24 may determine that pressure compensation is improper which is an indication that that one or more components of the patient circuit may have been changed without updating the patient information.

If processing unit 24 determines that pressure compensation to patient 10 is not improper at 48, the method proceeds to 50 where processing unit 24 controls pressure support device 4 to continue to provide pressure support therapy to patient 10. As long as processing unit 24 determines that pressure compensation to patient 10 remains proper, processing unit 24 repeats analyzing sensor data at 46 and determining whether pressure compensation to patient 10 remains proper at 48. Processing unit 24 may repeat 46 and 48 continually or at periodic intervals.

If processing unit 24 determines that pressure compensation to patient 10 is improper at 48, the method proceeds to 52 where processing unit 24 initiates action to confirm whether components of the patient circuit have been changed. Various types of actions may be initiated by processing unit 24 to confirm whether components of the patient circuit have been changed without departing from the scope of the disclosed concept.

In a non-limiting exemplary embodiment of the disclosed concept, processing unit 24 initiate action to have patient manually confirm the patient circuit information. For example and without limitation, processing unit 24 may control input/output device 26 to display one or more prompts to patient 10 and receive input from patient 10 in response to the prompts indicating whether one or more components of the patient circuit have been changed. Similarly, in a non-limiting exemplary embodiment of the disclosed concept, processing unit 24 may communicate with an external device (e.g., without limitation, a smart phone, tablet, computer, etc.) via communication unit 34 to have the external device display one or more prompts to patient 10 and receive input from patient in response to the prompts indicating whether one or more components of the patient circuit have been changed. The external device may communicate patient's 10 response back to processing unit 24.

In another non-limiting exemplary embodiment of the disclosed concept, processing unit 24 may initiate an auto-recognition routine to identify whether components of the patient circuit have changed. In this exemplary embodiment, processing unit 24 is able to communicate with various components of the patient circuit via communication unit 34. In the auto-recognition routine, processing unit 24 initiates communication with components of the patient circuit and, in turn, they respond with their corresponding patient circuit information. If the patient circuit information received from the patient circuit components is different than the patient circuit information stored in processing unit 24, the setting of pressure support device 4 will need to be updated.

In yet another non-limiting exemplary embodiment of the disclosed concept, processing unit 24 re-syncs patient circuit information with an external database. In this exemplary embodiment, patient circuit information is input to an external database. For example, a medical provider may keep an updated version of patient circuit information in an external database. In some cases, the medical provider may update the database, but fail to update the patient information and corresponding settings in pressure support device 4. In this case, processing unit 24 may re-sync patient circuit information with the external database by communicating with the external database via communication unit 34 and receiving the patient circuit information stored in the external database. Processing unit 24 may then store the received patient information so that the patient circuit information stored in processing unit 24 and the external database are the same.

In another non-limiting example embodiment, processing unit 24 may initiate action to confirm whether the patient circuit information has changed by alerting an equipment or medical provider. For example and without limitation, processing unit 24 may send an alert (e.g., without limitation, an e-mail, text message, or other type of alert) to an equipment or medical provider indicating that patient circuit components connected to pressure support device 4 may have been changed. The equipment or medical provider may, in turn, contact patient 10 to inquire whether components of the patient circuit have been changed and to arrange to have settings of pressure support device 4 updated.

After taking action to confirm whether patient circuit components have been changed, the method returns to 42 where processing unit 24 updates settings of pressure support device 4 based on patient circuit information in some exemplary embodiments of the disclosed concept. In some exemplary embodiments of the disclosed concept, processing unit 24 may not automatically return to 42. For example, processing unit 24 may notify an equipment or medical provider that components of the patient circuit may have changed. The equipment or medical provider may then manually update patient circuit information and initiate updating of setting of pressure support device 4.

By continually analyzing data and determining whether pressure compensation is improper, processing unit 24 may can identify when components of the patient circuit have changed without the need for input from patient 10. Processing unit 24 may also take action to confirm whether components of the patient circuit have changed and, in some exemplary embodiments, may automatically cause the patient circuit information in pressure support device 4 to gather updated patient circuit information and update its settings. Keeping patient circuit information and pressure support device 4 settings updated after a change in components of the patient circuit assists with providing optimal pressure support therapy.

The disclosed concept may also be applied to detect problems with components of the patient circuit. For example and without limitation, if a patient circuit includes a cushion that becomes torn, processing unit 24 may determine that the pressure compensation provided to patient 10 is improper. When steps are taken to confirm whether components of the patient circuit have changed, the medical provider or patient can confirm that proper pressure compensation cannot be provided due to the damage of a component of the patient circuit. The damaged component may then be identified and replaced.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support device for providing pressure support therapy to a patient, the pressure support device comprising:
   an airflow generator structured to generate pressure to provide pressure compensation to the patient via a patient circuit;
   one or more sensors structured to gather data related to effectiveness of the pressure compensation; and
   a processing unit structured to analyze outputs of the sensors while pressure support therapy is provided to the patient to determine if the pressure compensation provided to the patient is improper and to initiate action to confirm whether components of the patient circuit have been changed in response to determining that the pressure compensation provided to the patient is improper, and wherein, in response to determining that the pressure compensation provided to the patient is improper, the processing unit is structured to initiate communication with components of the patient circuit to determine whether any components of the patient circuit have changed.

2. The pressure support device of claim 1, wherein the one or more sensors include at least one sensor structured to gather data related to sleep-disordered breathing symptoms, and wherein the processing unit is structured to analyze outputs of the at least one sensor to determine whether sleep-disordered breathing symptoms are exacerbated and to determine that pressure compensation is improper based on the determination of exacerbated sleep-disordered breathing symptoms.

3. The pressure support device of claim 1, wherein the one or more sensors include at least one sensor structured to gather data related to a sub-optimal breath waveform shape, wherein the processing unit is structured to analyze the output of the at least one sensor to determine whether signs of uncomfortable breathing are present and to determine that pressure compensation is improper based on the determination of the presence of signs of uncomfortable breathing.

4. The pressure support device of claim 1, wherein the one or more sensors include at least one sensor structured to sense pressure proximate to a selected location in the patient circuit, wherein the processing unit is structured to compare the sensed pressure with a predicted pressure at the location in the patient circuit and to determine that pressure compensation is improper when the sensed pressure and the predicted pressure differ by greater than a predetermine threshold value.

5. The pressure support device of claim 1, wherein the one or more sensors includes an accelerometer structured to sense acceleration of the patient, wherein the processing unit is structured to compare the sensed acceleration with an expected range of values associated with the accelerometer and to determine that pressure compensation is improper when the sensed acceleration is outside the expected range.

6. The pressure support device of claim 1, wherein the processing unit is structured to analyze outputs of the one or more sensors over a period of time and to generate expected ranges of outputs corresponding to the one or more sensors based on their outputs over the period of time, and wherein the processing unit is structured to determine improper compensation based on outputs of one or more sensors being outside their corresponding expected range of outputs.

7. A pressure support device for providing pressure support therapy to a patient, the pressure support device comprising:
   an airflow generator structured to generate pressure to provide pressure compensation to the patient via a patient circuit;
   one or more sensors structured to gather data related to effectiveness of the pressure compensation; and
   a processing unit structured to analyze outputs of the sensors while pressure support therapy is provided to the patient to determine if the pressure compensation provided to the patient is improper and to initiate action to confirm whether components of the patient circuit have been changed in response to determining that the pressure compensation provided to the patient is improper, and wherein, in response to determining that the pressure compensation provided to the patient is improper, the processing unit is structured to communicate with an external database including information on components of the patient circuit to determine whether any components of the patient circuit have changed.

8. The pressure support device of claim 7, wherein the one or more sensors include at least one sensor structured to gather data related to sleep-disordered breathing symptoms, and wherein the processing unit is structured to analyze outputs of the at least one sensor to determine whether sleep-disordered breathing symptoms are exacerbated and to determine that pressure compensation is improper based on the determination of exacerbated sleep-disordered breathing symptoms.

9. The pressure support device of claim 7, wherein the one or more sensors include at least one sensor structured to gather data related to a sub-optimal breath waveform shape, wherein the processing unit is structured to analyze the output of the at least one sensor to determine whether signs of uncomfortable breathing are present and to determine that pressure compensation is improper based on the determination of the presence of signs of uncomfortable breathing.

10. The pressure support device of claim 7, wherein the one or more sensors include at least one sensor structured to sense pressure proximate to a selected location in the patient circuit, wherein the processing unit is structured to compare the sensed pressure with a predicted pressure at the location in the patient circuit and to determine that pressure compensation is improper when the sensed pressure and the predicted pressure differ by greater than a predetermine threshold value.

11. The pressure support device of claim 7, wherein the one or more sensors includes an accelerometer structured to sense acceleration of the patient, wherein the processing unit is structured to compare the sensed acceleration with an expected range of values associated with the accelerometer and to determine that pressure compensation is improper when the sensed acceleration is outside the expected range.

12. The pressure support device of claim 7, wherein the processing unit is structured to analyze outputs of the one or more sensors over a period of time and to generate expected ranges of outputs corresponding to the one or more sensors based on their outputs over the period of time, and wherein the processing unit is structured to determine improper compensation based on outputs of one or more sensors being outside their corresponding expected range of outputs.

* * * * *